(12) United States Patent
Sanborn et al.

(10) Patent No.: US 8,748,635 B2
(45) Date of Patent: Jun. 10, 2014

(54) METHOD FOR PREPARATION OF ANHYDROSUGAR ETHERS

(75) Inventors: Alexandra J. Sanborn, Lincoln, IL (US); Stephen J. Howard, Sherman, IL (US)

(73) Assignee: Archer Daniels Midland Company, Decatur, IL (US)

( * ) Notice: Subject to any disclaimer, the term of this patent is extended or adjusted under 35 U.S.C. 154(b) by 814 days.

(21) Appl. No.: 12/410,016

(22) Filed: Mar. 24, 2009

(65) Prior Publication Data

US 2009/0253920 A1 Oct. 8, 2009

Related U.S. Application Data

(60) Provisional application No. 61/038,950, filed on Mar. 24, 2008.

(51) Int. Cl.
| | | |
|---|---|---|
| *B01J 29/06* | (2006.01) | |
| *B01J 29/40* | (2006.01) | |
| *C07H 3/10* | (2006.01) | |
| *C07D 493/04* | (2006.01) | |

(52) U.S. Cl.
CPC . *C07H 3/10* (2013.01); *B01J 29/06* (2013.01); *B01J 29/40* (2013.01); *C07D 493/04* (2013.01)
USPC ........................................................ 549/464

(58) Field of Classification Search
None
See application file for complete search history.

(56) References Cited

U.S. PATENT DOCUMENTS

| | | | |
|---|---|---|---|
| 4,659,846 A | 4/1987 | Maurer et al. | |
| 4,770,871 A * | 9/1988 | Greenshields | 424/49 |
| 4,845,091 A | 7/1989 | Schönafinger et al. | |
| 4,976,965 A | 12/1990 | Block et al. | |
| 5,614,643 A | 3/1997 | Schneider et al. | |
| 5,635,588 A * | 6/1997 | Eshuis et al. | 528/395 |
| 6,608,167 B1 | 8/2003 | Hayes et al. | |

FOREIGN PATENT DOCUMENTS

EP 1 038 862 A2 9/2000

OTHER PUBLICATIONS

International Search Report and Written Opinion of the International Searching Authority issued in International Patent Application No. PCT/US2009/038113, mailed Nov. 10, 2009.

* cited by examiner

*Primary Examiner* — Sun Jae Yoo
(74) *Attorney, Agent, or Firm* — Mark W. Roberts; Alexandra Sanborn

(57) ABSTRACT

A method for alkylation of an anhydrosugar compound in which a dialkyl carbonate is reacted with an anhydrosugar compound in the presence of a solid phase basic catalyst. A typical anhydrosugar compound is anhydrosugar alcohol, a dianhydromonoether and mixtures thereof. The reaction step uses zeolyte as the solid phase basic catalyst. The zeolite catalyst is typically a zeolite having ammonium groups. The reaction is carried out at a temperature below 240° C. and the reaction time is 2 hours or less.

7 Claims, No Drawings

METHOD FOR PREPARATION OF ANHYDROSUGAR ETHERS

CROSS REFERENCE TO PROVISIONAL APPLICATION

This application is based upon and claims the benefit of priority from Provisional U.S. Patent Application No. 61/038,950 filed on Mar. 24, 2008, the entire contents of which are incorporated by reference herein.

FIELD OF INVENTION

This application pertains to a method for the preparation of anhydrosugar ethers by alkylation of anhydrosugar alcohols. In particular, the application relates to a process for alkylation of anhydrosugar alcohols using a solid phase basic catalyst.

BACKGROUND OF THE INVENTION

Natural products are a rapidly expanding field of study. There is increased concern by skilled artisans over the use and consumption of fossil-fuel based compounds. As a result, new ways to utilize renewable products are being examined in order to lower the environmental burden on the planet. 1,4:3,6-dianhydrohexitols are considered biomass-derived substances, in that they are obtained from natural products. 1,4:3,6-dianhydrohexitols are important starting materials and intermediates in various organic synthetic reaction schemes such as in the formation of numerous pharmaceutical compounds, in food production, cosmetic production, plastic and polymer production. One such class of derivatives of 1,4:3,6-dianhydrohexitols are ether derivatives. Ether derivatives of 1,4:3,6-dianhydrohexitols, such as isosorbide dinitrate, are useful as a medication to relieve the pain of angina attacks and to reduce the frequency of such attacks by improving blood flow to the heart. For example, U.S. Pat. No. 4,976,965 discloses a medicinal composition comprising a mixture of isosorbide nitrates and dihydropyridines, and an alkylene glycol ether.

Another important derivative is dimethyl isosorbide, which is useful as industrial solvents and pharmaceutical additives, as well as for use in personal care products. The structure of dimethyl isosorbide is shown below:

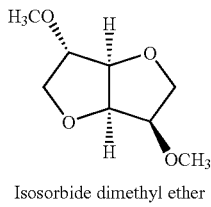 [SMILES: CO[C@H]1CO[C@H]2[C@@H]1OC[C@H]2OC]

Isosorbide dimethyl ether

Dianhydrosugar ethers are prepared by reacting alkyl halides and dialkylsulfates with an anhydrosugar such as isosorbide and isomannide, a 1,4:3,6-dianhydrohexitol, in the presence of a base or phase transfer catalysts such as tetra-n-butylammonium bromide, benzyltriethyammonium bromide or N-methyl-N,N-dioctyloctan-1-aminium chloride. However, these processes require a highly pure anhydrosugar starting material in order to achieve reasonable yields at to be cost effective.

There is a need for a simple and cost effective process for the production of very pure anhydrosugar ethers, at reasonable yields, without having to use pure anhydrosugar alcohols as the starting materials.

SUMMARY OF THE INVENTION

One aspect of this disclosure provides a method for the alkylation of anhydrosugar alcohols to form dianhydrosugar ethers using a solid phase catalyst.

In one embodiment, the method for alkylation of an anhydrosugar compound comprises a step of reacting a dialkyl carbonate with an anhydrosugar compound in the presence of a solid phase basic catalyst. The anhydrosugar compound is typically selected from the group consisting of an anhydrosugar alcohol, a dianhydromonoether and mixtures thereof. In certain embodiments, the alkyl component of the dialkyl carbonate comprises an alkyl group having 1 to 10 carbon atoms. For example, the alkyl group is one of methyl, ethyl, propyl and butyl. In one particular embodiment, the anhydrosugar compound is isosorbide.

The reaction step in one exemplary embodiment of the present disclosure uses zeolyte as the solid phase basic catalyst. In one embodiment, the zeolite catalyst is a zeolite having ammonium groups. In certain embodiments, the reaction is carried out at a temperature below 240° C. In addition, the reaction time is 2 hours or less.

Additional advantages and other features of the present disclosure will be set forth in part in the description which follows and in part will become apparent to those having ordinary skill in the art upon examination of the following or may be learned from the practice of the disclosure. The advantages of the disclosure may be realized and obtained as particularly pointed out in the appended claims.

As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

DETAILED DESCRIPTION OF THE INVENTION

This disclosure is directed to a method for of alkylating anhydrosugar alcohols using an alkyl carbonate as a starting material. In particular, this invention is directed to the production of dianhydrosugar ethers by reacting an anhydrosugar alcohol or ether with an alkyl carbonate in the presence of a solid phase catalyst.

Typical anhydrosugar compounds suitable for use as starting materials in the methods disclosed herein include dianhydrosorbitol (also known as isosorbide) and or dianhydromannitol (also known as isomannide) as well as other similar compounds known in the art. Examples of dianhydromonoethers prepared in accordance with the disclosure include isosorbide monoalkyl ether and isomannide monoalkyl ether. The anhydrosugar alcohols and dianhydromonoethers can be mixed and used as starting materials. The exemplary starting material is isosorbide because it is readily available or easily made from the dehydration of sorbitol. The dianhydrosugar compound can be a crude reaction mixture containing isosorbide.

The alkyl component of the alkyl carbonate is an alkyl having 1 to 10 carbon atoms. Examples of the alkyl component include methyl, ethyl, propyl and butyl. An exemplary alkyl carbonate is dimethyl carbonate.

The solid phase basic catalyst can be a zeolite catalyst or a strong base. The zeolite catalyst is a strongly basic zeolite catalyst bearing ammonium groups, but the catalyst may include base modified clays, aluminas, resins and silica gels. Representative examples of the zeolite catalyst include a ZSM-5 type zeolite catalyst such as CBV8014, CBV3024E, CBV2314, CBV5524E or CBV28014 from Zeoyst International, as well as ferrierite type catalysts such as CP914 and CP914C. The base can be sodium hydroxide, lithium hydroxide or lithium hydride. Generally, the stronger the base, the greater the yield of the dialkyl anhydrosugar ether.

A typical reaction scheme showing the conversion of isosorbide to isosorbide dialkyl ether with an alkyl carbonate reactant in the presence of zeolyte catalyst is shown below:

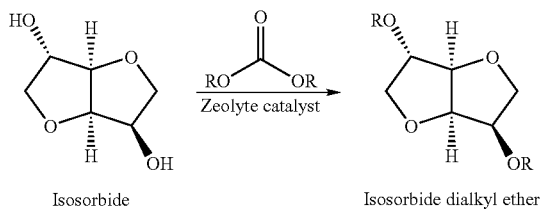

Isosorbide          Isosorbide dialkyl ether

The reaction disclosed herein has the advantage in that the method can be carried out batchwise, semi-batchwise, continuously or semi-continuously. Thus, many reactors are suitable for use with the inventive methods such as a slurry reactor, a fixed-bed reactor, a loop reactor. For example, the method may involve bubbling or feeding the dialkyl carbonate and anhydrosugar compound through a bed of the solid phase catalyst.

Another advantage of the present teaching is that the dialkyl carbonates react to give only volatile by-products, specifically alcohol and carbon dioxide, thus eliminating the need to employ filtration and extraction stages associated with conventional alkylating agents such as dialkyl sulfates and alkyl halides. The alcohol and carbon dioxide can be vented from the reactor to provide for greater yield by forcing the reaction to completion. Further, the dialkyl carbonates and solid phase catalysts are more adaptable for use in a continuous alkylation process and are not limited to batch processing only. The methods disclosed herein thus provide for an inexpensive and environmentally friendly biproducts and catalyst.

Not to be held by theory, the reaction of an anhydrosugar alcohol with alkyl carbonates in the presence of zeolyte likely occurs with the zeolyte removing the alcoholic hydrogen to create a negatively charged oxide. This oxide attacks the alkyl carbonate carbonyl carbon in a nucleophilic attack to create a negative charge on the carbonyl oxygen. The bonds then rearrange, the alkyl group transferring to the anhydrosugar oxygen thereby creating an ether, CO2 and an alcohol. A reaction scheme is shown below:

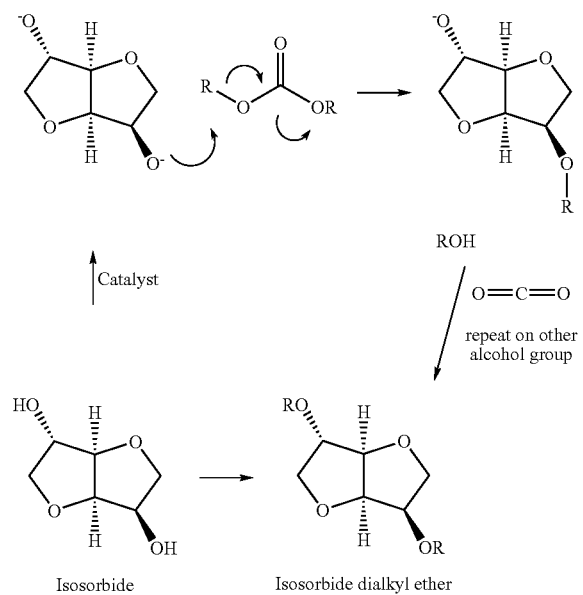

Isosorbide          Isosorbide dialkyl ether

The methods disclosed herein have the further advantage that the solid phase catalysts can be regenerated and recycled. Further, the reaction mixture can be recycled until an adequate amount of the dianhydrosugar ether is obtained. Thus, if the reaction fails to go to completion, the dianhydrosugar alcohol, monether or mixture thereof can be recycled and additional dialkyl carbonate added to the reaction mixture to continue to produce the dianhydrosugar diether. This eliminates the task of separating the unreacted starting material and intermediates such as dianhydrosugar alcohol monoether and dianhydrosugar monoether.

Another advantage of the method is that the reaction can be carried out at lower termperatures (200° C. or less) and for shorter reaction time (two hours or less) at atmospheric pressure. Conventional methods of preparing dianhydrosorbitol ethers using dialkyl carbonates require temperatures greater than 240° C., high pressure (at least 4 MPa) and reaction times that exceed 2 hours. Thus, the present invention provides for much milder reaction conditions.

The present teaching provides for easier isolation of products and separation of the catalyst from the reaction products. The dianhydrosugar ether products made in accordance with the methods disclosed herein may be further purified.

Thus, the present teaching provides a simple, clean and cost effective method of alkylating anhydrosugar compounds. Pure dianhydrosugar ethers can be obtained using dianhydrosugar alcohols contained in crude reactions mixtures as a starting material and it is not necessary to use pure dianhydrosugar alcohols as starting materials. Thus, the methods disclosed herein eliminate the task of obtaining a pure anhydrosugar alcohol for use as the source starting material.

The present disclosure can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the disclosure. However, it should be recognized that the present disclosure can be practiced without resorting to the details specifically set forth. In other instances, well known processing structures have not been described in detail, in order not to unnecessarily obscure the present disclosure.

Only a few examples of the present disclosure are shown and described herein. It is to be understood that the disclosure is capable of use in various other combinations and environments and is capable of changes or modifications within the scope of the inventive concepts as expressed herein.

EXAMPLE

The following example illustrates a specific embodiment of the method, but it is not to be considered as limiting the invention in any manner.

Isosorbide (30.24 g), CBV8014 zeolite (30 g) and dimethyl carbonate (300 mL) were placed in a one liter high temperature reactor (an Autoclave Engineers) and heated to 200° C. for two hours. The reaction produced both dimethylisosorbide and monomethyl isosorbide.

While this invention has been described with reference to several preferred embodiments, it is contemplated that various alterations and modifications thereof will become apparent to those skilled in the art upon a reading of the preceding detailed description. It is therefore intended that the following appended claims be interpreted as including all such alterations and modifications as fall within the true spirit and scope of this invention.

What is claimed is:

1. A method for alkylation of isosorbide comprising the step of reacting a dialkyl carbonate with isosorbide in the presence of a solid phase basic zeolite catalyst to form at least one of a monoalkyl- or dialkyl isosorbide ether.

2. The method of claim 1, wherein the alkyl component of the dialkyl carbonate comprises an alkyl group having 1 to 10 carbon atoms.

3. The method of claim 2, wherein the alkyl group is selected from the group consisting of methyl, ethyl, propyl and butyl.

4. The method of claim 2, wherein the alkyl group is methyl.

5. The method of claim 1 wherein the zeolite catalyst is a zeolite having ammonium groups.

6. The method of claim 1 or 5, wherein the reaction is carried out at a temperature below 240° C.

7. The method of claim 1 or 5, wherein the reaction is carried out at a temperature below 240° C. and the reaction time is 2 hours or less.

\* \* \* \* \*